United States Patent [19]

Tate et al.

[11] Patent Number: 5,208,150

[45] Date of Patent: May 4, 1993

[54] SALMONELLA-SELECTIVE PLATING MEDIUM

[75] Inventors: Christopher Tate, Frederick; Russell Miller, Glen Dale; Edward Mallinson, Columbia; Sammy Joseph, Derwood, all of Md.

[73] Assignees: The University of Maryland, College Park, Md.; The United States of America as represented by the Secretary of Agriculture, Washington, D.C.

[21] Appl. No.: 681,358

[22] Filed: Apr. 8, 1991

Related U.S. Application Data

[63] Continuation-in-part of Ser. No. 330,479, Mar. 30, 1989.

[51] Int. Cl.$^5$ .......................... C12Q 1/10; C12Q 1/04; C12Q 1/24; C12Q 1/02; C12Q 1/22; C12Q 1/06; C12Q 1/08; C12N 1/20

[52] U.S. Cl. ........................................ 435/38; 435/34; 435/30; 435/29; 435/31; 435/39; 435/40; 435/252.8

[58] Field of Search ........................ 435/36, 38, 34, 30, 435/29, 31, 39, 40, 252.8

[56] References Cited

U.S. PATENT DOCUMENTS 4,223,093 9/1980 Newman et al. .
4,308,347 12/1981 Forrer et al. .

OTHER PUBLICATIONS

Fisher Catalogue (1988) pp. 1521, 1520, 1458.
Miller (1990) Abstract Only.
The MD Poultryman UMd UMD, p. 2-7.
Sigma Catalogue (1992) pp. 939-940, 960-961.
Avian Diseases, vol. 25, No. 2, pp. 513-516, D. J. Kingston, "A Comparison of Culturing Drag Swabs and Litter for Identification of Infections with Salmonella SPP. in Commercial Chicken Flocks".
Applied Microbiology, vol. 17, No. 5, pp. 767-768, May 1964, R. M. Julseth, et al., "Effect of Temperature on Growth of Salmonella in Rehydrated Skim Milk from a Food-Poisoning Outbreak".
Applied Microbiology, vol. 23, No. 1., pp. 82-87, Jan. 1972, C. A. Dega, et al., "Growth of Salmonella Typhimurium in Skim Milk Concentrates".
Journal of Food Protection, vol. 47, No. 4, pp. 299-302, Apr. 1984, B. J. Juven, et al., "Recovery of Salmonella from Artificially Contaminated Poultry Feeds in Non-Selective and Selective Broth Media".
Feedstuffs, vol. 63, No. 4, pp. 40-44, Jan. 28, 1991, E. T. Mallison, "Salmonella: Novel Detection System Combines Reliability, Practicality".
Journal of Food Protection, vol. 45, No. 3, pp. 249-252, Feb. 1982, J. Y. D'Aoust, et al., "Surfactants for the Effective Recovery of Salmonella in Fatty Foods".
Review of Medical Microbiology, Seventeenth Edition, pp. 233-246, 1987, Jawetz et al., "Enteric Gram-Negative Rods (Enterobacteriaceae)".
Difco, Difco Manual, Tenth Edition, pp. 946-949, 275-277, 765-767 and 1128-1131, 1984.

*Primary Examiner*—Christine M. Nucker
*Assistant Examiner*—David R. Preston
*Attorney, Agent, or Firm*—Oblon, Spivak, McClelland, Maier & Neustadt

[57] ABSTRACT

An improved plating media incorporates TERGITOL®4, an alkyl sodium sulfate biological detergent, in a Xylose-lysine agar base. The plating media may also include peptone and sulfapyridine to further inhibit Citrobacter growth. The media is highly preferential for Salmonella, giving a greater number of Salmonella positives, and reduced competitive organisms. When incorporated with drag swab methodology employing skim milk or evaporated milk as a holding media, which may advantageously include novobiocin to suppress unwanted bacterial growth, coupled with a tetrathionate-culturing broth or other selective enrichment broth, the plating media completes a highly sensitive assay for the detection of Salmonella, particularly keyed for poultry and livestock handling structures, and for veterinary and human clinical laboratory applications.

18 Claims, No Drawings

SALMONELLA-SELECTIVE PLATING MEDIUM

This is a continuation-in-part application of U.S. patent application Ser. No. 07/330,479, filed Mar. 30, 1989. The entire disclosure thereof is incorporated herein by reference.

BACKGROUND OF THE INVENTION

1. Field of the Invention

This invention pertains to a Salmonella-preferential or selective plating medium, to be used in conjunction with assays conducted to determine the presence of Salmonella microorganisms in poultry facilities, other livestock species and man. More specifically, a plating medium derived from a Xylose-lysine agar base incorporates TERGITOL ®4 to selectively culture Salmonella organisms.

2. Background of the Patent Application

U.S. application Ser. No. 330,479 discloses an inventive assay for the detection of Salmonella in poultry facilities. The assay is characterized by the use of moistened drag swabs, which can be dragged or rubbed along the bedding, litter, floor or work surfaces of a poultry or livestock house during routine activities, and which are subsequently held in a holding media comprised of double-strength skim milk (2XSM). The holding medium, if maintained at reduced temperature, has demonstrated good maintenance of the bacterial colonies obtained, without loss of Salmonella populations, or overrepresentation. Upon collection of sufficient samples, the stored samples are transferred to a culture broth preferential for the growth of Salmonella organisms. Culture broths incorporating tetrathionate are preferred, in preferentially promoting the growth of Salmonella cultures. A representative culture broth is Hajna TT broth.

The culture broth may be assayed, directly, for the presence of Salmonella cultures by, e.g., DNA probes, an ELISA assay, or related immuno assay. In the alternative, and preferentially, a plating medium is used to further grow the cultures, to allow identification of the same by visual inspection.

This method, although slightly longer, taking up to 48 hours, is substantially less expensive, and permits the mass inspection of a large number of samples. The culture broth is plated onto traditional preferential growth media, disclosed in the parent application as including Xylose-lysine-deoxycholate, and in the alternative, plain brilliant green (BG) agar growth media. Both these media, as well as other suitable media, are supplemented with novobiocin, in ranges sufficient to ensure preferential Salmonella growth. The novobiocin may also be incorporated in the culture broth, to improve results, in a range of 1-50 micrograms/ml, preferably 15-30 micrograms/ml.

While the above test that is the subject of the parent application presents many advantages over conventional tests, the preferred plating assay is sensitive to the use of plating media that are not sufficiently preferential for Salmonella to ensure detection of virtually all the Salmonella organisms present in poultry and livestock production and processing facilities, food processing facilities and human populations.

3. Background of the Prior Art

There are a wide variety of commercially available plating media on the market, suggested as being preferential for Salmonella. Yet, these media are not sufficiently reliable to ensure detection of in excess of 90% of Salmonella positive samples. Six samples having been previously determined, by another laboratory as negative for Salmonella were in fact positive for a variety of Salmonella serotypes using the improved plating medium of the invention described below. The particularly dangerous serotype Salmonella enteritidis was isolated from 1 of the 6 samples. This potential for complete misses leaves poultry and livestock manufacturers and veterinary and medical laboratories with a false sense of security, posing potentially disastrous consequences.

Accordingly, a need continues to exist for a highly Salmonella-preferential plating media that can be used in conjunction with assays of the prior art, and the assay described above, incorporating the holding media 2XSM. Due to the limited availability of double strength skim milk, it would additionally be desirable to find alternative, readily available holding media providing the same advantages.

SUMMARY OF THE INVENTION

Applicants have discovered that the addition of TERGITOL ®4 (7-ethyl-2-methyl-4-undecanol hydrogen sulfate, or sodium salt thereof) available from Sigma (TERGITOL ®4 is a trademark of Union Carbide Corporation) to conventional media such as Xylose-Lysine agar base medium (XL agar, Difco, Detroit, Mich.) with the addition of H2S indicators eliminates many Salmonella competitors, allowing superior detection of Salmonella colonies obtained from drag swabs and other environmental samples forming colonies on the plating media. Additionally, repeated tests with other plating media showed an extremely high isolation of Salmonella colonies, in excess of 98% of all positive samples. Peptone and sulfapyridine can be added to increase selectivity. Sulfapyridine suppresses the competition Citrobacter, while peptone enhances Salmonella growth.

The plating media can be readily incorporated with the drag swab sampling assay that is the subject of parent application U.S. application Ser. No. 330,479. The inventors have also discovered that an alternative holding medium to double strength skim milk is commercially available evaporated skim milk. Thus, evaporated milk such as that marketed by Carnation gives results essentially equivalent to that of the double strength skim milk. As the product is substantially less expensive, and readily available, it provides a desirable alternative. A sterile can opener must be used, and the top of the can disinfected, and the evaporated milk must be determined to be free of bactericidal agents.

DETAILED DESCRIPTION OF THE INVENTION

The addition of TERGITOL ®4 (7-ethyl-2-methyl-4-undecanol hydrogen sulfate, or sodium salt) to conventional Salmonella-preferential plating media significantly improves the Salmonella-selectivity of the plating media. Conventional acceptable media include XL agar, available from Difco, Detroit, Mich. An ideal medium has a high number of positives detected, and very few competitor colonies plated out. Other media may be used in place of conventional plain XL agar bases. TERGITOL ®4 (T4) concentrations in the agar media may vary, depending on the agar type, and predominant colonies. Concentrations at 2-30 ml/liter (1) of agar appear to be appropriate for most conventional Salmonella-selective plating media. A preferred range is 3 ml/l–12 ml/l. T4 is autoclave-stable, and has no special storage requirements. It should be noted, however, that certain concentrations of T4 may be antagonistic to certain elements of available agars, the result of adding certain concentrations of T4 thereto, being an increase in competing organisms.

Although the T4 can be added to existing commercially available -Salmonella-preferential media, the Xylose-lysine agar base may be prepared directly, with the T4 added thereto. Incompatible bases will be detected by routine plating experiments.

An exemplary preparation of the inventive plating medium is given below. Amounts may be adjusted as required.

TABLE 1

PREPARATION: XLT4 AGAR (1) Weight out 47 g of plain xylose-lysine (XL) and (no desoxycholate) agar base (Difco, catalog #0555-01-8).
(2) To the 47 g of XL agar add 0.8 g ferric ammonium citrate, 6.8 g sodium thiosulfate and 3.0 g bacto agar (additional).
(3) Add ingredients to 1 L of distilled water in a 2 L or larger Erlenmeyer flask. Mix well using a magnetic stir-bar.
(4) Add 4.6 ml of TERGITOL ® 4 (Sigma #T-8256) and mix again.
(5) Isotherm (flowing steam) for 10 minutes, or heat on a hot plate to near boiling.
(6) Remove and mix again for three minutes.
(7) Autoclave for 12 minutes at 118° C., 13 psi pressure. Higher autoclave temperatures may lead to some media precipitates.
(8) Remove and cool in a water bath to 45-50° C.
(9) Mix again gently for three minutes (vigorous mixing can cause foaming).
(10) Pour plates (the plates may appear dark at first but should lighten after being refrigerated). The finished medium should be 4–5 mm thick. Use 18–20 ml per standard plate. If plates are too thin the $H_2S$ positive (black colony) characteristics of salmonella will be suppressed and/or delayed.
(11) Allow plates to remain at room temperature overnight to allow some drying before refrigeration at 2–5° C.
(12) Remove plates from refrigerator for 24 hours for further drying prior to use.

Poured XLT4 agar plates appear to have a shelf life of at least three months when stored in a refrigerator in closed plastic bags.

As indicated above, the T4-containing plating media are highly preferential for Salmonella, suppressing the growth of virtually all other gram-negative competing bacteria, to the extent that simple inspection can reveal the presence of Salmonella, as opposed to other organisms. The growth characteristics of various gram-negative bacteria on XLT4 (Xylose-lysine TERGITOL ®4) growth medium are set forth in Table 2.

TABLE 2

GROWTH CHARACTERISTICS OF VARIOUS GRAM-NEGATIVE BACTERIA ON XLT4 MEDIUM
Plates Incubated at 35° C. for 24 Hours
(Results essentially the same in 48 Hours)

| ORGANISM | GROWTH |
| --- | --- |
| Salmonella spp. (numerous) | Good, black colonies |
| Salmonella enteriditis ($H_2S$-positive strain) | Good, black colonies |
| Salmonella enteriditis ($H_2S$-positive strain) | Good, pinkish-yellow colonies |
| Proteus mirabilis | No growth |
| Proteus vulgaris | No growth |
| Pseudomonas aeruginosa | Slight (haze of growth at point of inoculation) |
| Pseudomonas putrefaciens | No growth |
| Providencia stuartii | No growth |
| Providencia rettgeri | Slight (haze of growth at point of inoculation) |
| Citrobacter freundii ($H_2S$-positive strain) | Fair, no black production (yellow colonies) |
| Hafnia alvei ($H_2S$-positive strain) | Fair, no black production (yellow colonies) |
| Morganella morganii | Poor |
| Enterobacter aerogenes | Poor |
| Escherichia coli | Slight (haze of growth at point of inoculation |
| Acinetobacter calcoaceticus | No growth |

The agar plating media that is the subject of this invention is superior in the suppression of non-Salmonella organisms that mask the presence of clinically significant numbers of Salmonella, and also permits good growth of Salmonella colonies, providing for detection of the same, when compared with available agar medium. As reflected in Table 3, the TERGITOL ®4-containing media (XLT4) of the invention identified far more Salmonella positive samples (98%) when compared to other available commercial types. Another way of expressing the presence or absence of a competitive colony in a selective media is the purity score for the media, where a score of 1 gives very low plate purity of Salmonella species, with a high number of competing colonies, while a score of 4 represents extremely high plate purity. Of course, the higher the plate purity, the fewer the problems encountered in identifying false positives, and recovery of the Salmonella. As shown in Table 4, the agar of the invention is dramatically superior in both the detection of Salmonella-positive cultures, and the purity score, when compared with other plating media.

TABLE 3

LAYER FLOCKS - ENVIRONMENTAL DRAG SWAB SAMPLES
ADDITIONAL DATA - 1989 - 1990

| DIAG # | # OF SAMPLES | # OF SALMONELLA POSITIVE SAMPLES | SALMONELLA DETECTED MEDIA TYPE | | | | |
| --- | --- | --- | --- | --- | --- | --- | --- |
| | | | XLT4 | XLD | XLDN | BGA | BGAN |
| 798C | 6 | 6 | 5 | 0 | 2 | 5 | 6 |
| 844C | 12 | 11 | 11 | 4 | 8 | 10 | 9 |
| 847C | 20 | 20 | 20 | 3 | 14 | 15 | 16 |
| 848C | 13 | 13 | 13 | 2 | 12 | 7 | 11 |
| 852C | 10 | 10 | 10 | 3 | 8 | 4 | 7 |
| 855C | 10 | 8 | 7 | 2 | 7 | 4 | 6 |
| 856C | 20 | 17 | 17 | 8 | 15 | 16 | 17 |
| TOTALS | 91 | 85 | 83 | 22 | 66 | 61 | 71 |
| % OF NUMBER OF POSITIVE | — | — | 98 | 26 | 78 | 72 | 85 |

TABLE 3-continued
LAYER FLOCKS - ENVIRONMENTAL DRAG SWAB SAMPLES
ADDITIONAL DATA - 1989 - 1990

| | | # OF SALMONELLA | SALMONELLA DETECTED MEDIA TYPE | | | | |
|---|---|---|---|---|---|---|---|
| DIAG # | # OF SAMPLES | POSITIVE SAMPLES | XLT4 | XLD | XLDN | BGA | BGAN |
| SAMPLES DETECTED | | | | | | | |

TABLE 4
PLATING MEDIA EFFICIENCY IN DETECTING 196 TRUE SALMONELLA-POSITIVE CULTURES OF DRAG SWAB SAMPLES

| AGAR MEDIA | POSITIVES DETECTED | PURITY SCORE* |
|---|---|---|
| Xylose-lysine-tergitol-4 | 98 | 3.7 |
| Brilliant Green-novobiocin | 91 | 2.9 |
| Plain Brilliant Green | 82 | 2.7 |
| Xylose-lysine-desoxychloate-novobiocin | 81 | 2.3 |
| Brilliant Green-sulfadiazine** | 72 | 1.5 |
| Plain Xylose-lysine-desoxycholate | 33 | 1.2 |
| Hektoen Enteric** | 20 | 1.0 |
| MacConkey** | 12 | 1.0 |

*Average score of 1 represents very low plate purity while 4 represents high plate purity (freedom from competitor problems and ease of recovering salmonella).
**Only 25 positive samples were available for comparisons of Brilliant Green-Sulfadiazine, Hektoen Enteric and MacConkey agars.

Competitive colonies of Citrobacter can be further inhibited by the addition of peptone and sulfapyridine to the media. Preferred ranges for peptone and sulfapyridine in the media are 1-10 g/l and 0.2-1 g/l, respectively.

As noted, the XLT4 can be used directly particularly in a clinical veterinary and human setting as a conventional plating medium. However, in conjunction with the drag swab assay discussed above, employing a holding medium of double strength skim milk, coupled with a tetrathionate based culture broth, the claimed invention provides superior results. Thus, samples of the poultry facility are initially obtained by dragging or rubbing swabs, or similar fabric or absorbent devices, about the surfaces of the poultry or livestock facility. The swabs are advantageously moistened with the holding media which encourage adhesion of small potentially Salmonella contaminated particles. Applicants have discovered that in addition to double strength skim milk, evaporated milk provides an excellent holding medium. Provided the evaporated milk is free of bactericidal agents, and opened and poured from the commercial container under sterile conditions, this offers a less expensive, readily available and used holding medium.

In an alternative embodiment, the plating medium may be presented as a freeze-dried or dehydrated powder. The powder is incorporated in a liquid-absorbing matrix, such as a sponge. The loaded matrix can be used as a media base under a filter such as filter paper on which liquid biological sample is placed. The liquid sample is absorbed on the matrix, reconstituting the media. Biological microorganism contaminants are retained on the filter, and derive nutrient from the media through the filter. An apparatus of this type is addressed in U.S. Pat. No. 4,829,005. The media, either in conventional form, or freeze dried and incorporated in a matrix, may be advantageously substituted for the conventional media recited in U.S. Pat. No. 4,829,005. When dehydrated, the media is preferably prepared without agar, which may complicate reconstitution.

The inventors have further discovered that the assay of the parent application, U.S. application Ser. No. 330,479 can be further improved by the addition of novobiocin, an antibiotic, to the holding media, be it skim milk or evaporated milk. Concentrations of the antibiotic may range from 5-50 micrograms/ml of holding media and preferably at 15-30 micrograms/ml. The antibiotic is particularly effective in reducing Proteus and other non-Salmonellae contaminants, and thus can be advantageously added to the holding media, which, coupled with the low temperature at which the holding media is maintained, improves the static maintenance of the bacteriological entities of interest in the swab, and holding media.

As noted above, the parent application advantageously discloses the use of a tetrathionate culture broth, which is plated out on the plating medium of the invention.

Thus a superior plating medium for the detection of Salmonella from any collection assay includes a Xylose-lysine agar, such as the commercial available XL agar, supplemented with T4 in amounts of 2-30 ml/l of agar. The plating media is further improved by the addition of a H2S indicator.

A superior assay comprises dragging or rubbing swabs moistened with double strength skim milk or evaporated milk over the working surfaces of a poultry or other livestock growing or production facility, and holding the swabs in the double strength skim milk or evaporated milk as a holding medium, at reduced temperature, until sufficient swabs are collected for assay. These swabs are introduced to a culture broth, which is preferential for Salmonella, such as tetrathionate-containing Hajna TT broth, or other conventional broths, such as Muller-Kauffman tetrathionate broth. To further improve the selectivity of the assay, novobiocin may be added to the holding media, prior to culturing.

The cultured broth is plated out on the T4-containing media. Such an assay provides a rapid, automatable assay system for the detection of Salmonella, with a high degree of reliability, problems presented by competitive growths being substantially reduced. In practice, false negative results constitute no more than 2% of the samples tested when plated on the medium, using the described assay, and over 90% of Salmonella positive samples are detected.

The plating medium of the invention can advantageously be supported on dipslides comprised of an inert (e.g., plastic) substrate which supports a plurality of different media along one or both major surfaces. These dipslides can advantageously be used to polarize a single liquid sample and a variety of different media simultaneously and under identical conditions, to determine the presence and identity of various microorganisms in the sample.

The above invention has been described with reference to both generic description and by specific example. Alternatives will occur to those of ordinary skill in the art, particularly in the selection of base agars, holding media, plating media and the like, without the exercise of inventive faculty, and without departing from the scope of the invention, save as limited by the claims set forth below. Additionally, concentrations, unless indicated to the contrary are provided for the guidance of the experimenter, and are not absolute. Appropriate concentrations can be routinely determined.

What is claimed is:

1. In a Salmonella-selective plating medium, the improvement comprising the addition of 7-ethyl-2-methyl-4-undecanol hydrogen sulfate, or sodium salt (TERGITOL ®4) thereof, in concentrations sufficient to suppress Salmonella-competing organism growth.

2. The plating media of claim 1, wherein said plating media is a Xylose-lysine agar.

3. The plating media of claim 2, wherein said TERGITOL ®4 is present in a concentration of 2-30 ml/l of media.

4. The plating media of claim 2, wherein said TERGITOL ®4 is present in an amount of 3-12 ml/l of media.

5. The plating media of claim 2, wherein said media further comprises an H$_2$S indicator.

6. The plating media of claim 2 wherein said media further comprises peptone and sulfapyridine.

7. The plating media of claim 6, wherein peptone is added at 1-10 g/l and sulfapyridine is added at 0.2-1 g/l.

8. The plating media of claim 1, in dehydrated powder form.

9. The media of claim 8, said media being free of agar.

10. A plating media preferential for Salmonella organisms wherein said media comprises L-lysine, xylose, agar and TERGITOL ®4.

11. A plating media preferential for Salmonella organisms wherein said media comprises:
L-lysine,
Xylose,
agar,
TERGITOL ®4 in an amount of 2-30 m/l, and
peptone in an amount of 1-10 g/l and sulfapyridine in an amount of 0.2-1 g/l.

12. A plating media wherein the plating media comprises:
L-lysine,
Xylose,
TERGITOL ®4 in an amount of 2-30 m/l, and
peptone in an amount of 1-10 g/l and sulfapyridine in an amount of 0.2-1 g/l.

13. A plating media of claim 12 wherein the plating media is in a dehydrated form.

14. A method for monitoring structures housing poultry and/or livestock for Salmonella contamination, comprising:
A) periodically collecting drag swab samples dragged or rubbed along the surfaces of said structure,
B) maintaining said drag swabs in a holding medium liquid comprised of a milk product selected from the group consisting of skim milk, double strength skim milk, evaporated milk and mixtures thereof, at a reduced temperature until sufficient swabs are collected for culturing,
C) transferring said swabs to a culture broth which supports maintenance of Salmonella cultures, and culturing said swabs for a period of time sufficient to promote the multiplication of any Salmonella organisms captured in said drag swabs at a temperature conducive to the growth of said Salmonella organisms, and
D) plating said cultured broth onto the plating media of claim 1, allowing Salmonella organisms contained in said broth to grow on said media for a period of at least 20 hours, and identifying the number of Salmonella colonies grown thereon.

15. The process, of claim 14, wherein said holding media further comprises novobiocin.

16. The process of claim 14, wherein said media comprises a H$_2$S indicator.

17. The process of claim 14 wherein said media comprises peptone and sulfapyridine.

18. A dipslide comprising a biologically inert substrate and a plurality of plating medium at separate locations on said substrate, at least one of said plating media locations bearing the plating media of claim 1.

* * * * *